United States Patent
Myers et al.

(10) Patent No.: US 9,390,237 B2
(45) Date of Patent: Jul. 12, 2016

(54) TEST STRIP AND METHODS AND APPARATUS FOR READING THE SAME

(71) Applicant: MicroLab Devices Limited, Yeadon, Leeds (GB)

(72) Inventors: Thomas Oliver Myers, Leeds (GB); Thomas Oliver Davies, Rugby (GB)

(73) Assignee: MICROLAB DEVICES LIMITED (GB)

( * ) Notice: Subject to any disclaimer, the term of this patent is extended or adjusted under 35 U.S.C. 154(b) by 0 days.

(21) Appl. No.: 14/646,698

(22) PCT Filed: Nov. 22, 2013

(86) PCT No.: PCT/GB2013/053084
§ 371 (c)(1),
(2) Date: May 21, 2015

(87) PCT Pub. No.: WO2014/080212
PCT Pub. Date: May 30, 2014

(65) Prior Publication Data
US 2015/0286803 A1    Oct. 8, 2015

(30) Foreign Application Priority Data
Nov. 22, 2012    (GB) .................................. 1221015.9

(51) Int. Cl.
*G06F 17/00* (2006.01)
*G06F 19/00* (2011.01)
(Continued)

(52) U.S. Cl.
CPC .......... *G06F 19/366* (2013.01); *G01N 21/8483* (2013.01); *G06T 7/0012* (2013.01)

(58) Field of Classification Search
CPC ..................................................... G06F 19/366
USPC ............................................ 235/375, 462.15
See application file for complete search history.

(56) References Cited

U.S. PATENT DOCUMENTS

| 6,295,506 | B1 | 9/2001 | Heinonen et al. |
| 7,344,081 | B2 * | 3/2008 | Tseng ................ G01N 21/8483 |
| | | | 235/375 |

(Continued)

FOREIGN PATENT DOCUMENTS

| DE | 102010021491 A1 | 12/2011 |
| EP | 2453242 A1 | 5/2012 |

(Continued)

OTHER PUBLICATIONS

International Preliminary Report on Patentability and Written Opinion of the International Searching Authority, International Application No. PCT/GB2013/053084, dated May 26, 2015, 14 pgs.

(Continued)

*Primary Examiner* — Seung Lee
(74) *Attorney, Agent, or Firm* — Faegre Baker Daniels LLP

(57) ABSTRACT

Embodiments of the present invention provide a method of analyzing a response of an analyte test device, comprising recording, by a device reading device, an image of coded test information associated with the test device, determining, based directly on the image of the test information, one or more test parameters, recording, by the reading device, an image of one or more optically responsive portions of the test device, and determining the response of the test device based on the one or more test parameters and the image of the one or more optically responsive portions of the test device.

20 Claims, 5 Drawing Sheets

(51) Int. Cl.
*G06T 7/00* (2006.01)
*G01N 21/84* (2006.01)

(56) References Cited

U.S. PATENT DOCUMENTS

| | | | |
|---|---|---|---|
| 8,638,441 B2 * | 1/2014 | Egan | G01N 21/8483 356/246 |
| 2002/0002326 A1 | 1/2002 | Causey, III et al. | |
| 2006/0210435 A1 | 9/2006 | Alavie et al. | |
| 2006/0222567 A1 | 10/2006 | Kloepfer et al. | |
| 2007/0231922 A1 | 10/2007 | Petruno et al. | |
| 2007/0273928 A1 | 11/2007 | Robinson et al. | |
| 2009/0306543 A1 | 12/2009 | Slowey et al. | |
| 2010/0254581 A1 | 10/2010 | Neeser et al. | |
| 2012/0038820 A1 | 2/2012 | Kempahonnaiah | |
| 2012/0075626 A1 * | 3/2012 | Geva | B01L 3/5023 356/244 |
| 2012/0106811 A1 | 5/2012 | Chen et al. | |
| 2012/0109688 A1 | 5/2012 | Yoo | |
| 2012/0122236 A1 * | 5/2012 | Tarpey | G01N 21/8483 436/501 |
| 2012/0178101 A1 | 7/2012 | Bae et al. | |
| 2012/0189509 A1 | 7/2012 | Hsiao | |
| 2013/0221090 A1 * | 8/2013 | Hensel | G06K 7/10722 235/375 |

FOREIGN PATENT DOCUMENTS

| | | |
|---|---|---|
| JP | 2003043051 A | 2/2003 |
| WO | 2006106084 A1 | 10/2006 |
| WO | 2006120656 A1 | 11/2006 |
| WO | 2009054729 A1 | 4/2009 |
| WO | 2012038146 A1 | 3/2012 |

OTHER PUBLICATIONS

International Search Report issued by the International Searching Authority, mailed Jul. 8, 2014, for International Application No. PCT/GB2013/053084; 6 pages.

Search Report issued by UK Patent Office for Application No. GB1221015.9, dated May 15, 2013, 3 pages.

* cited by examiner

TEST STRIP AND METHODS AND APPARATUS FOR READING THE SAME

RELATED APPLICATIONS

The present application is the national phase of International Application No. PCT/GB2013/053084, titled "TEST STRIP AND METHODS AND APPARATUS FOR READING THE SAME", filed on Nov. 22, 2013, which claims priority to British patent application No. GB1221015.9 filed on Nov. 22, 2012, the entire disclosures of both applications are incorporated herein by reference.

BACKGROUND

Test strips are often used for testing for the presence of an analyte of interest. The analyte may be, without limitation, a compound, virus, bacteria, protein etc. A sample to be tested is applied to the test strip. The test strip comprises one or more measurement regions where a response of the test strip to the sample is visibly observed. In some instances the sample is a fluid. However the sample may also be a solid, such as a powder. The term "test strip" may be used interchangeably to describe a device which contains at least one colour change region in response to an analyte and therefore may include a microfluidic cartridge.

In order to measure the response of the test strip to the sample the colour change may be analysed by eye as often the case in a pH test, however, such an approach only provides for a subjective determination. For a quantifiable output the test strip may be inserted into a dedicated reading device where it is subjected to predetermined illumination conditions so that the response of the measurement region(s) can be measured. However such dedicated test strip reading devices are expensive and require the user to have access to the dedicated equipment.

It is also known to use a non-dedicated reading device for reading a test strip. US2006222567 discloses a testing device for use with a mobile processing device such as a mobile phone having a camera to capture an image of an analyte reaction product. Software executing on the mobile phone determines the presence or quantity of the analyte in the reaction product from the image. As noted in paragraph 103 of this document, the software is specifically adapted for performing the analyte test.

US 2007/0273928 discloses a test strip which includes a grey scale calibration pattern which corresponds to one of 49 calibration codes. A memory module of a reading device includes a grey scale permutation matrix with a plurality of calibration codes by which a calibration of the test strip may be determined. However, the reading device requires the permutation matrix and knowledge of a test to be performed.

It is an object of embodiments of the invention to at least mitigate one or more of the problems of the prior art.

SUMMARY OF THE INVENTION

According to aspects of the present invention there is provided methods and apparatus as defined in the appended claims.

According to an aspect of the present invention there is provided a method of analysing a response of an analyte test device, comprising recording, by a reading device, an image of coded test information associated with the test device, determining, based on the image of the test information, one or more test parameters, recording, by the reading device, an image of one or more optically responsive portions of the test device, and determining the response of the test device based on the one or more test parameters and the image of the one or more optically responsive portions of the test device.

According to an aspect of the present invention there is provided an analyte test device, comprising one or more regions optically responsive to at least one analyte; and coded test information provided on the test device for providing one or more test parameters to a reading device.

According to an aspect of the present invention there is provided a reading device for analysing a response of an analyte test device, comprising an imaging device for recording images, a software module which, when executed by a processor of the reading device is arranged to determine one or more test parameters based on an image of coded test information associated with a test device, and to determine a response of the test device based on the one or more test parameters and an image of one or more optically responsive regions of the test device.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
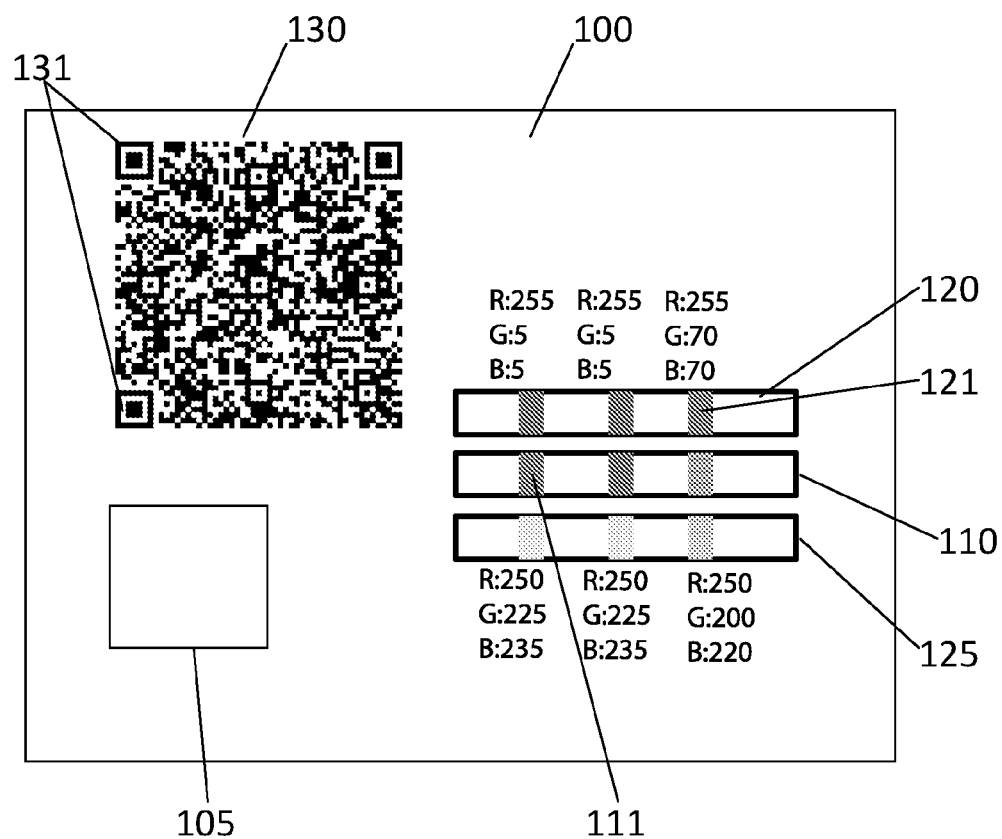
FIG. 1 shows an overview of a typical "test strip"

FIG. 1 illustrates an embodiment of the invention where the test strip is based on a lateral flow test device 100. However, it will be realised that other test strips may be envisaged which do not use fluidic samples.

The device 100 comprises a sample receiving area 105. A fluid sample, such as blood, urine, saliva etc. is applied to the sample receiving area 150. The sample receiving area 105 includes a porous membrane to at least partially retain an excess of the fluid sample. Although not shown, the device 100 comprises a labelling area into which some of the sample fluid is drawn by capillary action for a target analyte in the sample fluid to be tagged or labelled. The sample fluid may be drawn from the sample receiving area 105 to the labelling area by one or more porous pathways in the device 105. The porous pathways continue through the labelling area to allow the labelled sample fluid to be drawn to a responsive area 110. The responsive area 110 comprises one or more capture areas 111 in which a capture molecule has been immobilised. The responsive area 110 in FIG. 1 comprises three capture areas 111, although only one is specifically identified for clarity. The capture molecule is provided for binding to the target analyte and label complex. Owing to an accumulation of the complex bound in the capture area in some embodiments a colour change of the capture area 111 can be observed indicative of the presence of the target analyte. The device 100 may comprise a capture area 111 which captures any particle and is thus indicative of the operation of the device rather than the presence of the target analyte The device 100 further comprises first and second calibration regions 120, 125, although it will be realised that other numbers of calibration regions may be provided. In this exemplary case, the calibration regions 120, 125 define high and low colour bounds, respectively, for the responsive area 110. Each calibration region may comprise one or more optical reference areas 121, only one of which is specifically identified for clarity. Although the embodiment shown in FIG. 1 comprises two calibration regions 120, 125 it will be appreciated that embodiments may be envisaged having zero or one or more calibration regions 120, 125. Each of the references areas 121 in FIG. 1 is associated with a corresponding textual indication printed on the device 100 of the RGB values of the reference area, although it will be realised that this textual indication may be omitted in some embodiments.

In the embodiment shown in FIG. 1 each capture area 111 is provided with two corresponding optical reference areas 121 arranged either side of the corresponding capture area 111. One of the references areas is arranged to provide an optical reference for a low marker response level i.e. this colour would be associated with the minimum concentration of the analyte and the other reference area is arranged to provide an optical reference for a high marker response level i.e. this colour would be associated with the maximum concentration of the analyte. The optical reference areas 121 may be manufactured from the same material or substance as the corresponding capture area such that the reference area reacts in a similar manner to the capture area in the presence of variable environmental conditions such as illumination conditions. In other embodiments the reference areas may be manufactured from other materials to have a colour offset e.g. offset RGB value determinable as will be described.

In other embodiments the capture area 111 may fluoresce following capture of the target analyte. Some designs of diagnostics and immunoassays are suited to using fluorescent probes, rather than collidial beads. In these embodiments the capture area 111 exhibits a fluorescent response following capture of the target analyte, wherein a stokes shift may be used to measure the fluorescent response. The test strip itself may be provided with the necessary items to create an excitation signal, which may be of narrow wavelength, from an ambient light source. Alternatively the reading device may provide the excitation wavelength and read the emitted response.

It will be appreciated that embodiments of the invention may be used with test devices having a structure other than as previously described. For example embodiments of the invention may be used with a microfluidic test platform comprising one or more microfluidic channels in which colour changes and separations occur from the Ultra-violet to the Infra-Red wavelength regions.

Figure 2:
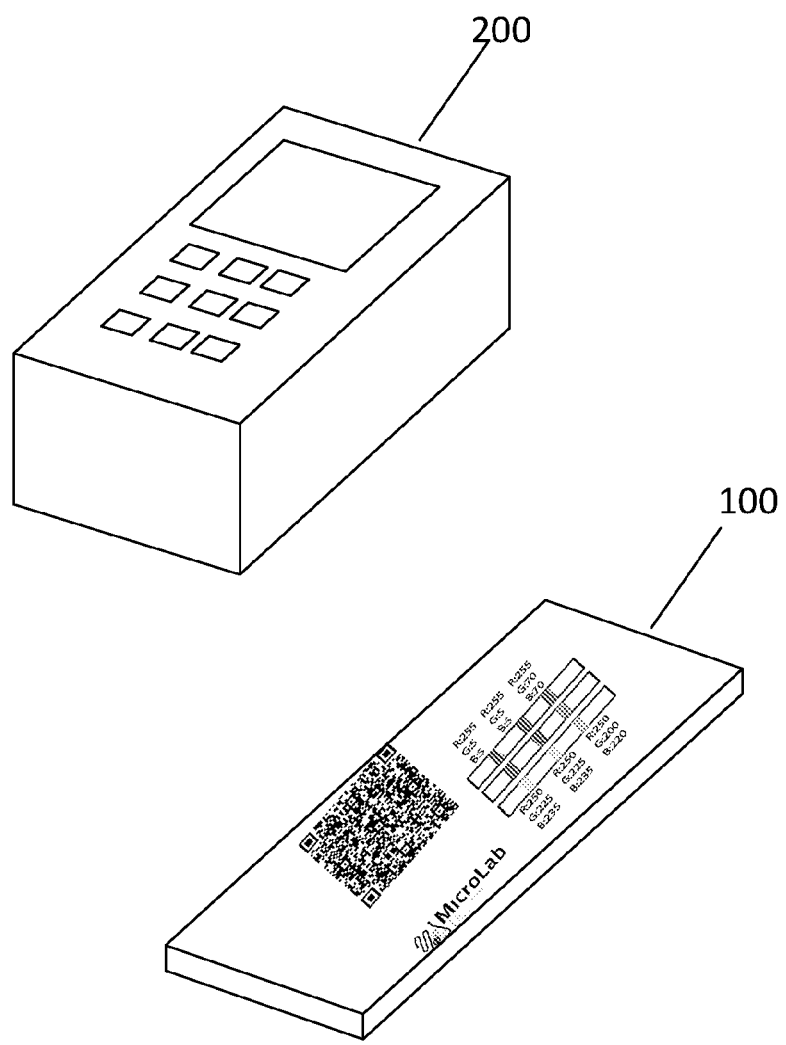
FIG. 2 shows an application of how a reading device may be presented to the test strip.

The device 100 comprises a test information region 130 for providing test information to a test reading device 200 as shown in FIG. 2. The test information region 130 is provided on a surface (the upper surface in FIG. 1) of the test device 100 for the reading device 200 to optically determine the test information there-from. The test information region is optically coded to provide the test information in a machine-readable form i.e. the test information is not human-readable. In some embodiments the test information region 130 is provided in the form of a matrix barcode such as a Quick Response (QR) code as shown in FIG. 1, although it will be realised that other types of matrix code may be used.

Some embodiments of the invention may be read by mounting the test device 100 in a holder affixed or forming part of the reading device 200. The holder may be arranged to retain the test device 100 in a predetermined position with respect to an optical detector of the reading device. In this case, the location of the various parts of the test device 100 will be known or controlled with respect to the detector. However other embodiments of the invention may be read by a reading device 200 whose position is not fixed with respect to the test device 100, as shown in FIG. 2. The reading device may thus be hand-held with respect to the test device 100. These embodiments of test device may comprise one or more optical registration marks 131 for allowing the position and/or orientation of the test device 100 to be determined by the reading device. In some embodiments the registration marks 131 form part of the test information region 130, such as forming part of the QR code. However in other embodiments the registration marks may be separate from the test information region 130.

The test information is arranged to provide test information to the reading device 200, as noted above. Advantageously, in some embodiments, the reading device 200 needs no prior knowledge of the test strip 100, the information and data it contains within it or the outputs that are required to be provided to the user. Embodiments of the invention may be used with non-dedicated reading devices 200 i.e. generic reading devices which are not specifically constructed for the purpose of reading test devices. Such reading devices 200 may be a mobile telephone, a smart phone, personal digital assistant, handheld computing device and the like. Such devices comprise, or are communicably coupleable to, a camera for providing image data relating to the test device 100. Software, such as an application or "app" executing on the reading device 200 is provided for receiving the image data of the test device 100 and interpreting the same. In the first instance, the reading device 200 may only require software to read the QR code. By scanning the QR code a portion of the QR code may provide a URL directing the user to download a suitable analysis app. In embodiments of the invention the test information 130 provides the software executing on the reading device 200 with one or more test parameters for interpreting the image data such that the software is not required to include or access, e.g. via a wireless data link, the test parameters. In this way, the test information 130 provides the test parameters directly to the reading device 200 without the reading device being required to access a data source for the test information. It will be realised that the reading device 200 may compute one or more test parameters based on test information 130. However it is not necessary to use the test information to access a data source such as a database to obtain the test parameters. Advantageously this allows generic test software to be used on the test device. By generic it is meant that the test software does not comprise, prior to reading the test device 100, the test parameters. Furthermore, the reading device 200 does not require a data connection in use.

In particular, the test information 130 according to embodiments of the invention comprises threshold information indicative of one more threshold values for a condition. The threshold information may define a lower threshold for the condition, upper and lower thresholds for the condition, an upper threshold for the condition or a combination thereof for one or more conditions, as will be explained.

In an embodiment of the invention the test information 130 is arranged to be readable by the reading device 200 to provide a series of values each separated by a predetermined character, such as "/" although it will be realised that other characters may be chosen. The test information may define:

A/B/C/D

Where A is a lower threshold value for a first condition, B is a lower threshold value for a second condition, C is an upper threshold value for a third condition and D is a lower threshold value for a third condition. The test information may be arranged according to a predetermined structure or format. For example, the first value (A) may provide the lower value for the first condition, the second value (B) may provide the lower threshold value for the second condition etc., wherein the structure is provided to the test device in advance. Alternatively, the format of the threshold information may also be encoded into the test information. For example, the test information 130 may provide a series of values in the form 1L/2L/3U/3L where the number indicates the condition and U or L indicate upper or lower, respectively.

In an embodiment of the invention the test information 130 contains algorithm information indicating an algorithm to be applied to the capture areas 111. For example, outcome 1 may result if the individual capture areas 111 meet the test:

If ((peak 1<4) & (peak2<5) & (peak3>100))

then perform outcome 1.

This algorithm information is provided by the optically coded test information 130. In one embodiment this may be coded, subsequently read and used as a string. In other embodiments the basic framework of each test could be loaded i.e. they are all if-then tests and then individual logical operators are substituted to construct individual algorithms for each outcome.

The test information 130 may further include output information indicative of a textual output to be displayed by the reading device 200 when the responsive area 111 of the test device 100 corresponds to one or more threshold values of the test information. For example, the test information 130 may comprise output information such as characters indicative of the output "Discharge/Reassure" which are to be displayed when a responsive area, or a combination of areas, results in a particular algorithm outcome. This has added advantages that the reading or user interaction software is not specific to a language or terminology, but the test strip determines the language and phraseology to use.

In some embodiments of the invention the test information 130 may further comprise ID information indicative of the identification of the test device 100. The ID information may be comprised of first and second parts wherein the first part identifies a type of test device 100 and the second part uniquely identifies either the particular test device 100 or a batch from which the test device originated.

The test information 130 may further provide configuration information. In one embodiment the configuration information defines one or more of: a number of capture areas on the test device; a target colour of the capture area(s) i.e. an expected colour of the capture area; reading device setup information defining, for example characteristics of illumination to be provided by the reading device; a number of calibration regions 120, 125; whether external illumination is required to read the test device 100; a desired illumination level of the external illumination; a value indicative of whether an auxiliary command is to be used, the auxiliary command being indicative of one or more further commands being provided to the reading device; and the one or more auxiliary commands themselves. For example, an auxiliary command value of 1 may indicate a first encoding format of the test information 130 using a predetermined algorithm of the reading software in combination with test values from the test information 130.

Figure 3:
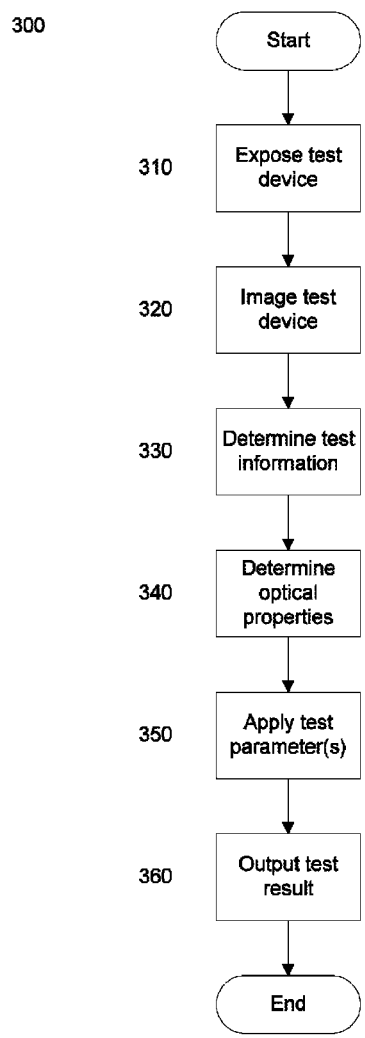
FIG. 3 shows a flow chart of the sequence of events to read the test strip.

FIG. 3 illustrates a method 300 according to an embodiment of the invention.

In step 310 the test device 100 is exposed to a sample. Exposing the test device 100 to the sample may comprise placing the test device in, or placing in contact with the receiving area 105. Where the sample is a fluid sample the fluid may be brought into contact with the receiving area 105 such that at least a portion of the fluid sample is absorbed by the membrane of the receiving area 105. Subsequent to the fluid sample being brought into contact with the receiving area 105 some of the fluid sample is drawn through the labelling area to the responsive area 110. One or more of the capture areas 111 in the responsive area 110 change their optical properties, such as colour, in response to the presence of the labelled sample fluid. In other embodiments the test strip 100 may be based on a gas, powder or solid.

In step 320 the test device 100 is imaged by the reading device 200. The imaging of the test device 100 may comprise inserting the test device 100 into a holder associated with the reading device 200 i.e. to maintain the test device 100 in a predetermined position in relation to the reading device 200. However in other embodiments the test device 100 is imaged whilst a user holds the reading device 200. The user may be required to hold the reading device 200 at an approximate distance to the test device 100 which may be indicated by a display screen of the reading device displaying a graphical indication and a real-time image of the test device 100 such that the user may align the graphical indication with the test device 100 by viewing the display screen.

During step 320 the reading device 200 may illuminate the test device 100, for example using a light emitter such as an LED. The light emitter may be an on-board flash (with or without filtration) of the mobile telephone. The illumination may be visible or invisible to the human eye. The reading device 200 is positioned to be able to capture an image of the capture area 111 and the test information 130. The image of the capture area 111 and the test information 130 may be recorded as a single image, i.e. containing both features, or they may be separately imaged i.e. each recorded as a single image by the reading device 200. It will be appreciated that, in some embodiments, step 330 may be followed by step 320, or step 320 then 330. In some embodiments a single image is taken capturing both the test information 130 and responsive and calibration regions. In some embodiments the test information 130 will be read, unbeknown to the user, to determine any special reading/imaging requirements of the test strip before capturing images of the responsive regions. Depending on the embodiment, the QR code 130 may be read and then the user instructed to image the responsive region 110 using the attained configuration data.

In step 330 the test information is determined by the reading device 200. Step 330 may comprise determining one or more test parameters from the test information 130 by the reading device 200, as described above. In some embodiments step 330 comprises determining an ID of the test device 100 from the test information, configuration information, threshold information and algorithm information. Step 330 comprises the software executing on the reading device 200 interpreting the image data relating to the test information 130 to determine the one or more test parameters and test device ID. As described above, the test parameters define one or more parameters relating to the response of the capture area 111 to the target analyte.

In step 340 one or more optical properties of the test device 100 are determined. In step 340 the optical properties of the one or more capture areas 111 are determined. Step 340 comprises the software executing on the reading device determining the properties of the capture area 111 from the image relating to the responsive area 110. The optical properties may comprise determining a hue of each capture area, where the hue may be determined as colour values, such as RGB values, for the capture area 111. The optical properties of the one or more optical reference areas 121 may also be determined in step 340. The same optical properties determined for the capture area may be determined for the optical reference areas 121 in step 340. For example, step 340 may comprise determining a hue of each optical reference area 121. From the respective optical properties of the capture area 111 and the one or more optical reference areas 121, a relative hue between the capture area 111 and the corresponding one or more optical reference areas 121 may be determined. The relative hue may indicate a difference in colour between the capture area 111 and the reference area 121. In some embodiments the configuration data may provide one or more scaling values indicative of a colour change of the capture area against concentration of target analyte. Using the one scaling value(s) the relative hue measurements may be transformed into a value with units, for example, ng/ml which is indicative of the concentration of the target analyte in the sample. These values then are inserted into the outcome algorithm as part of the processing described in relation to step 350.

In some embodiments, steps 320, 330 and 340 may be repeated to obtain a plurality of images of the one or more responsive areas 110 and calibration regions 120, 125. It will also be appreciated that one image may include a plurality of responsive areas 110 which are separately analysed. The software executing on the reading device 200 associates the images and determined optical properties from each of the plurality of images with the test device 100 based upon the test information 130. In particular the software determines the ID of the test device from the test information and stores the determined optical properties associated with the ID of the test device 100 such that multiple images may be captured to improve a reliability of the optical measurements. A mean value of the optical properties for the capture area(s) and reference area(s) may then be used in subsequent steps.

In step 350 the test parameters are applied to the properties determined in step 340. The software determines an outcome of the test based on the application of the test parameters to the determined optical properties of the capture area 111, which as described may be determined in combination with the optical properties of one or more reference areas.

In step 360 a result of the test is output to the user. The result may be output as a textual output provided on the display screen of the reading device 200. However other outputs, such as an audible output, are also envisaged and colour indicators, such as a Red or Green box may be provided. The result to be output may be derived from the test information 130 as described above. In some embodiments, the result of the test may be transmitted to a remote computing device, such as a server. In some embodiments, the test results may be accompanied by the one or more properties determined in step 340. The test results may be stored at the remote server for analysis.

Figure 4:
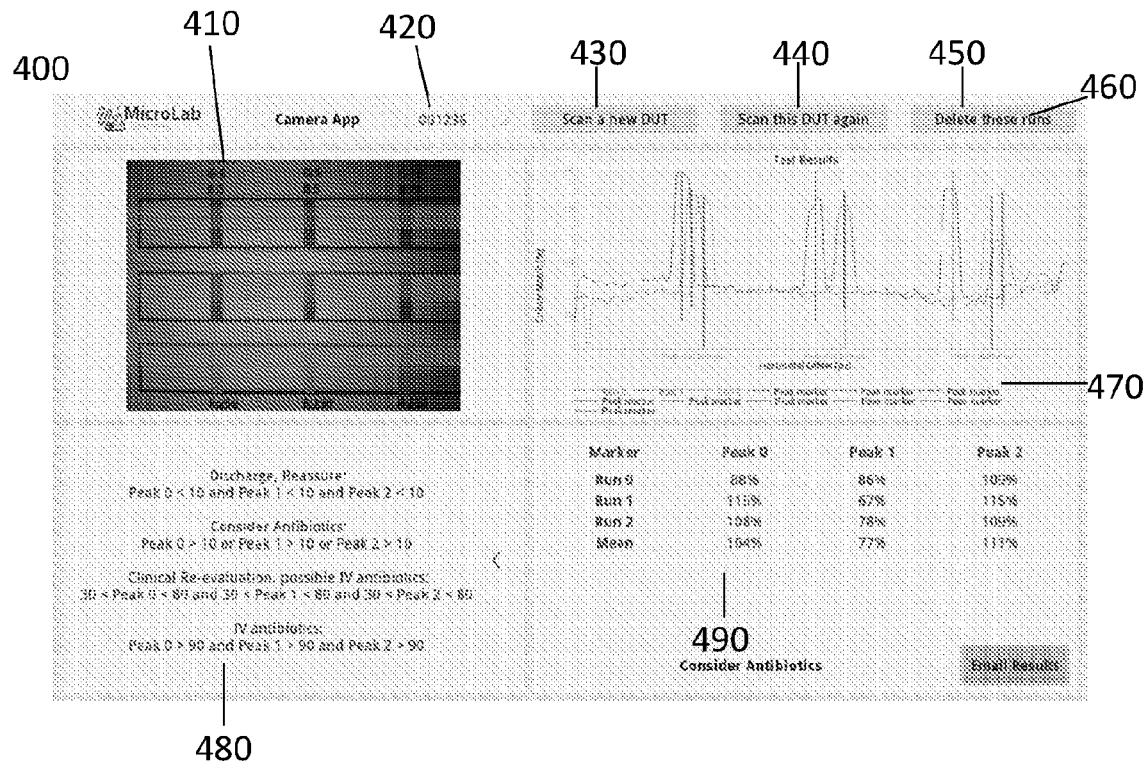
FIG. 4 shows a typical user interface showing the results from the test strip on a mobile computing device.

FIG. 4 illustrates an example screenshot 400 output on the display of the reading device 200. The screenshot 400 includes an image 410 of the responsive region 110 and the calibration regions 120, 125. Whilst capturing the image the image 410 may be provided in real time to the user to enable accurate location of the test device 110 with respect to the reading device 200 camera. However once one or more images have been captured the image 410 may be a stored image. The screenshot 400 further comprises an indication of the test device ID 420 as determined from the test information 130. Graphical controls 430, 440 450 are provided to the user enabling control of the reading device 200 and software. Control 430 enables the scanning or recording of a new test device; control 440 enables a further scan or recording of the present test device 100; and control 450 enables the deletion of any previous recordings of the current test device 100.

A graphical representation 460 of the optical properties is provided for the user's information. The graphical representation may indicate the absolute and/or relative colour levels of the capture areas 111. In one embodiment the graphical representation may indicate as a percentage a relative colour between high and low reference areas. In the displayed example the optical properties of a test device 100 having three capture areas 111 is shown.

Region 470 provides a textual or readable indication of the optical properties of the test device 100 for each image thereof. As previously described, the test device 100 may be recorded multiple times in order to determine average optical properties. Region 470 indicates the relative hue of each capture area for each recording and an average value thereof.

Region 480 indicates the algorithm and test parameters obtained from the test information 130 of the test device 100 for the user's information. In the example shown the algorithm comprises four outcome constructions or possibilities each having their own set of associated test parameters. These constructions are read from the optically encoded region as previously described.

An outcome of the test, based on the algorithm and test parameters shown in region 480 and recorded optical properties 470, is provided to the user as a textual indication 490. Based on the indication the user may take appropriate action.

In some embodiments of the invention the test information 130 is arranged to provide location information. The location information is indicative of a location of one or more features of the test device 100, such as a location of the responsive areas 110 of the test device 100. It will be realised that the location of other features may also be provided. The location may be defined with respect to a location of the test information 130 on the test device 100. That is, the location information may be relative with respect to the location of the test information 130. The location information may provide a position of the one or more responsive areas 110, such as comprising one or more of a distance of the responsive area from the test information 130 and an angle between an axis of the test information 130 and the one or more responsive areas 110. In some embodiments the location information is utilised by the reading device 200 as a location in which to perform a search for the feature, such as the responsive region 110, as will be explained. By providing the location information the reading device 200 is able to quickly locate the one or more features such as responsive regions 110, with minimal computation expenditure.

Figure 5:
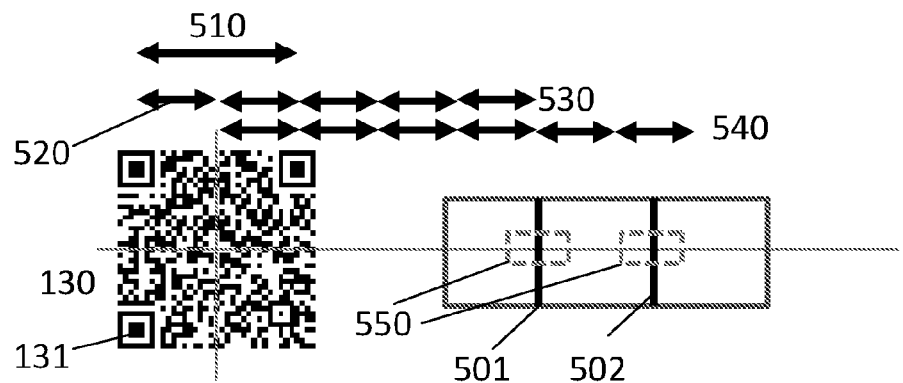
FIG. 5 provides an illustration of location information according to an embodiment of the invention.

Referring to FIG. 5, there is illustrated test information 130 as previously described and first and second responsive areas 501, 502 of a test device. The location information provided by the test information 130 may be used to determine a location of the first and second responsive areas 501, 502. It will be realised that the location information may provide a location of other features of the device. In particular, the test information 130 may provide a distance of the one or more responsive areas 501, 502 from the test information 130. The distance may be based on a size of the test information 130. In this way, since in some embodiments a position of the device 100 may not be constrained relative to the reading device 200, for example a height or distance between the device 100 and the reading device 200 may vary, a differing number of pixels in an image of the device may also vary. The use of a unit of measurement based on a size of the test information 130 accounts for such variations.

The location information may be defined in terms of a number of pixels used to capture the image of the test information 130. In particular in some embodiments a number of pixels between first and second registration marks 131 of the test information 130. The reading device 200 is arranged to determine a length 510 of the test information 130 between the first and second registration marks 131 as shown in FIG. 5, which may be referred to as a "barcode length" 510. In some embodiments a unit of measurement 520 used to determine the location of one or more features of the device 100 is determined there-from. The unit of measurement may be referred to as a "barcode width" 520. The unit of measurement may be determined as half of the barcode length 510, although it will be realised that other units based on the distance between the first and second registration marks 131 may be determined. In the exemplary embodiment shown in FIG. 5 the location information provides a first distance 530 to a first 501 responsive area and a second distance 540 to a second responsive area 502 of the device 100. In the example the first distance 530 is four measurement units 530 or barcode widths and the second distance 540 is 5.5 measurement units. The distance may be determined relative to a centre of the test information 130.

In some embodiments, the location information provides an initial estimate of the location of one or more features of the device 100. Using this for the accurate analysis of the markers, however, may problematic since the test information 130 may be inaccurately located with respect to the feature(s). For example the test information may be an adhesive label relatively inaccurately placed on a test device 100. Therefore the location information may provide an approximate location in which to search for the respective feature.

In one embodiment, a search process performed by the reading device 200 is based on one or more search regions 550 as shown in FIG. 5 denoted by the locations provided by the location information. In other embodiments the search is used to find "mechanical" features of the device, such as the rim of a region which encapsulates all the colour change regions. Whilst the search regions 550 are shown as rectangular in FIG. 5 it will be realised that they may be other shapes, such as circular. In one embodiment the test information 130 may provide a search radius within which the reading device 200 is to perform a search for a respective feature.

Using a feature detection technique, such as a Harris detector, FAST-ER or AGAST, the reading device 200 may be used to search the one or more regions 550 to determine an exact location of the features within the search regions 550. It will also be appreciated that other feature detection techniques may be used.

Figure 6:
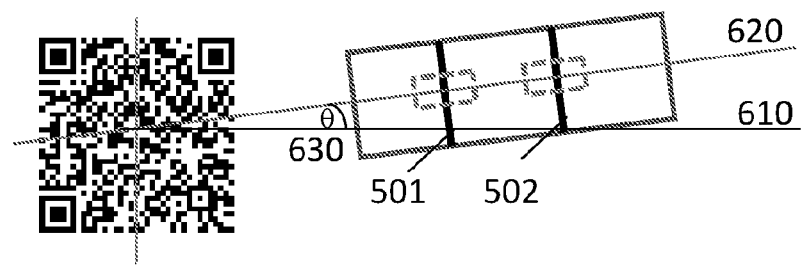
FIG. 6 provides a further illustration of the location information according to another embodiment of the invention.

Referring to FIG. 6, in some embodiments the location information may provide angular information to identify a location of one or more features of the device 100. The one or more features may be the one or more responsive areas 501, 502, although the location other features may be provided. The angular information may provide an angle θ 630 between a reference line 610 and a line 620 intersecting the one or more features such as responsive areas 501, 502. The reference line 610 may be defined as a line parallel with an axis of the test information 130 such as defined by registration marks 131 of the test information 130.

As described above, location information provides a location of one or more features of the device to the reading device 200. However it can be appreciated that the location of the reading device 200 with respect to the test device 100 may vary. In particular, an angle may exist between the reading device 200 and test device may exist when an image is recorded. This angle provides a "perspective" to the image of the test device 100. In some embodiment the software executing on the reading device 200 comprises a perspective transform. The perspective transform is used by the reading device 200 to convert the locations of one or more features in the image to a standard coordinate system, regardless of the effect of translation and rotation of the test device 100 with respect to the reading device 200. The perspective transform is a mathematical operation applied to an image to allow for warping of the image such that it appears to be viewed from another position. This allows the reading device 200 to be held at various attitudes with respect to the test device 100. The perspective transform function corrects for this translation by using the registration marks 131 and distance points identified by the test information 130 to calculate and correct for the angle, thus the image to be analysed is transformed mathematically to reconstruct the image as if it were imaged perfectly perpendicular. If this was not corrected then features positions would be "cast" and the locations inaccurate.

In some embodiments the test information 130 may comprise colour analysis information. In one embodiment the colour analysis data defines what colour region to read in a particular marker, for example, ff0000 would indicate to read Green and Blue channels with a 16 bit resolution. The colour analysis information may provide information defining how to relate the coloured measured to SI units, such as a ratio of colour change to response. For example a light red, of a predetermined colour value, may represent 1 ng/ml whereas a dark red, having another colour value, 14 ng/ml. The colour value of the responsive region may be scaled according to a predetermined equation which may be a polynomial equation, although other equations may be used.

Figure 7:
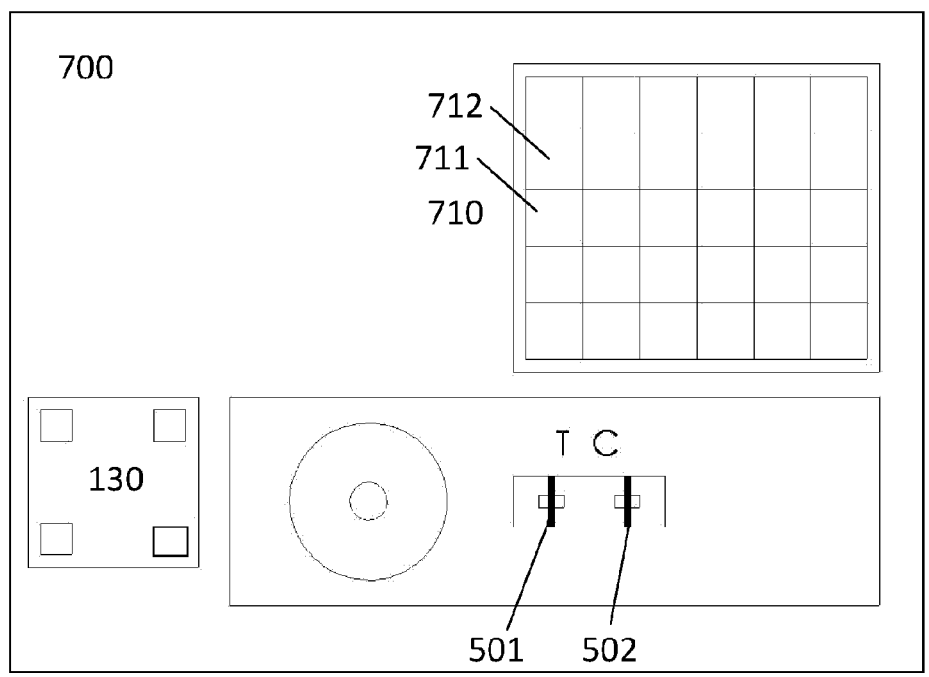
FIG. 7 illustrates a test device according to a further embodiment of the invention.

Referring to FIG. 7 a test device 700 according to an embodiment of the invention is shown. The test device 700 may be as previously described. The test device further comprises a reference colour region 710 which provides one or more reference colours 711, 712 (only two of which are numbered in FIG. 7 for clarity). The reference colour region 710 is used to provide one or more coloured regions based on which lighting conditions and a response of an imaging device of the reading device 200 may be determined. The test information 130 comprises colour information associated with the one or more one or more reference colours 711, 712. The colour information may provide information identifying a location of the one or more reference colours 711, 712 on the test device, such as described above, and information identifying a true colour of each reference colour 711, 712 in a predetermined colour space. The colour space may be one of CIE L*a*b, CIE XYZ, or sRGB. The colour information allows the reading device 200 to compare an observed colour of each of the reference colours 711, 712 with the actual colour to determine differences due to, for example, lighting conditions.

Using an appropriate mathematical technique, such as a matrix inversion, and assuming that the lighting and camera apply approximately linear effects to the colours in the image, the reading device 200 can calculate an effect of the lighting and camera on the colours in the image, and therefore calculate what the colours of the markers would have been, under standard lighting conditions and using a reference camera. In essence, controlled lighting and camera parameters are replaced with weakly controlled lighting an unknown camera and mathematical techniques used to account for them based on the colour information reference colour region.

It will be appreciated that embodiments of the invention allow a generic reading device 200 to be used with a variety of different test devices 100 each having an associated response characteristic. The reading device 200 is not required to possess or to obtain, for example, test parameters for interpreting the results of the test device 100 since, in embodiments of the invention, these are obtained from the test device. Advantageously this enables the use of general purpose handheld devices, such as a mobile phone or tablet computer, to act as a reading device. The software executing on the reading device is not required to be updated or to include knowledge of the response of the test device before reading the test device.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of analysing a response of an analyte test device, comprising:
   recording, by a reading device, an image of coded test information associated with the test device;
   determining directly based on the image of the test information one or more test parameters, wherein the test parameters comprise location information for providing a location on the test device of one or more features;
   recording, by the reading device, an image of one or more optically responsive portions of the test device; and
   determining the response of the test device based on the one or more test parameters and the image of the one or more optically responsive portions of the test device, wherein the determining the response comprises applying a perspective transform to the image of the one or more optically responsive portions of the test device based on the location information.

2. The method of claim 1, wherein the perspective transform is a mathematical operation applied to the image of the optically responsive portions, such that the image appears to be viewed from another position.

3. The method of claim 1, wherein the test information comprises first and second registration marks.

4. The method of claim 3, wherein the perspective transform corrects for an attitude between the reading device and the test device based on the registration marks and distance points identified by the test information.

5. The method of claim 1, wherein the location information provides one or more of a distance and an angle between the test information to the one or more features.

6. The method of claim 5, wherein the distance is determined based on a length between first and second registration marks.

7. The method of claim 1, wherein the location information provides an initial estimate of a location of the one or more features of the test device.

8. The method of claim 7, comprising performing, by the reading device, a search process based on one or more search regions denoted by the location information.

9. The method of claim 7, wherein the test information provides a search radius within which the reading device is arranged to perform a search for a respective feature.

10. The method of claim 7, wherein the reading device is arranged to use a feature detection technique such as a Harris detector, FAST-ER or AGAST.

11. The method of claim 1, wherein the optically responsive portions are arranged to one of change colour and fluoresce in the presence of the analyte.

12. A reading device for analysing a response of an analyte test device, comprising:
    an imaging device for recording images;
    a software module which, when executed by a processor of the reading device is arranged to directly determine one or more test parameters based on an image of coded test information associated with a test device, wherein the parameters comprise location information for providing a location on the test device of one or more features, and to determine a response of the test device based on the one or more test parameters and an image of one or more optically responsive regions of the test device, wherein the determining the response comprises applying a perspective transform to the image of the one or more optically responsive portions of the test device based on the location information.

13. The reading device of claim 12, wherein the perspective transform is a mathematical operation applied to the image of the optically responsive portions, such that the image appears to be viewed from another position.

14. The reading device of claim 12, wherein the perspective transform corrects for an attitude between the reading device and the test device based on one or more registration marks and distance points identified by the test information.

15. The reading device of claim 12, wherein the location information provides one or more of a distance and an angle between the test information to the one or more features.

16. The reading device of claim 15, wherein the distance is determined based on a length between first and second registration marks.

17. The test device of claim 12, wherein the coded test information comprises configuration information for configuring a reading device to record the image of the one or more optically responsive portions of the test device.

18. The test device of claim 12, wherein the coded test information is provided by an optically readable data code.

19. The reading device of claim 12, wherein the software module is arranged to determine threshold information indicative of one or one or more test thresholds for the optically responsive portions based the test parameters, and to determine the response of the test device is based on the one or more test thresholds.

20. The reading device of claim 12, wherein the software module is arranged to record an image of one or more calibration regions, and to determine the response of the test device based in part on the image of the one or more calibration region.

* * * * *